United States Patent
Royer et al.

(10) Patent No.: US 10,975,438 B2
(45) Date of Patent: Apr. 13, 2021

(54) METHODS AND COMPOSITIONS FOR PREDICTING CHRONIC LUNG ALLOGRAFT DYSFUNCTION

(71) Applicants: INSERM (Institut National de la Santé et de la Recherche Médicale), Paris (FR); Centre National de la Recherche Scientifique, Paris (FR); Université de Nantes, Nantes (FR); Centre Hospitalier Universitaire de Nantes, Nantes (FR)

(72) Inventors: Pierre-Joseph Royer, La Montagne (FR); Antoine Magnan, Nantes (FR); Sophie Brouard, Sucé-sur-Erdre (FR); Richard Danger, Rezé (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR); UNIVERSITÉ DE NANTES, Nantes (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 0 days.

(21) Appl. No.: 16/331,792

(22) PCT Filed: Sep. 7, 2017

(86) PCT No.: PCT/EP2017/072503
§ 371 (c)(1),
(2) Date: Mar. 8, 2019

(87) PCT Pub. No.: WO2018/046615
PCT Pub. Date: Mar. 15, 2018

(65) Prior Publication Data
US 2019/0226027 A1  Jul. 25, 2019

(30) Foreign Application Priority Data
Sep. 8, 2016 (EP) .................................. 16306125

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

2016/0002726 A1  1/2016 Keshavjee et al.

OTHER PUBLICATIONS

Kastelijn, E. A., et al., "Systemic and exhaled cytokine and chemokine profiles are associated with the development of bronchiolitis obliterans syndrome," Journal of Heart and Lung Transplantation 2010;29(9):997-1008.
Zhang, H., et al., "The Blk pathway functions as a tumor suppressor in chronic myeloid leukemia stem cells," Nature Genetics 2012;44(8):861-871.
Safavi, S., et al., "De novo donor HLA-specific antibodies predict development of bronchiolitis obliterans syndrome after lung transplantation," Journal of Heart and Lung Transplantation 2014;33(12):1273-1281.
Salama, M., et al., "Endothelin-1 is a useful biomarker for early detection of bronchiolitis obliterans in lung transplant recipients," Journal of Thoracic and Cardiovascular Surgery 2010;140(6):1422-1427.
Elidemir, O., et al., "105: Elevation of serum KL-6 can predict development of bronchiolitis obliterans syndrome in lung transplant recipients," Journal of Heart and Lung Transplantation 2007;26(2):S97.
International Search Report and Written Opinion of the International Searching Authority issued on International Application No. PCT/EP2017/072503 (dated Nov. 15, 2017).

*Primary Examiner* — Jehanne S Sitton
(74) *Attorney, Agent, or Firm* — Kenealy Vaidya LLP

(57) ABSTRACT

Some embodiments are directed to a prognostic method for determining whether a subject is at risk of having the CLAD, comprising: measuring the expression level of POU2AF1 or BLK in a biological sample obtained from the subject; comparing the expression level of POU2AF1 or BLK with a predetermined reference value and concluding that the subject is at risk of having CLAD when the expression level of POU2AF1 or BLK is lower than the predetermined reference value.

7 Claims, 3 Drawing Sheets

B

C

METHODS AND COMPOSITIONS FOR PREDICTING CHRONIC LUNG ALLOGRAFT DYSFUNCTION

FIELD OF THE INVENTION

Figure 1A:
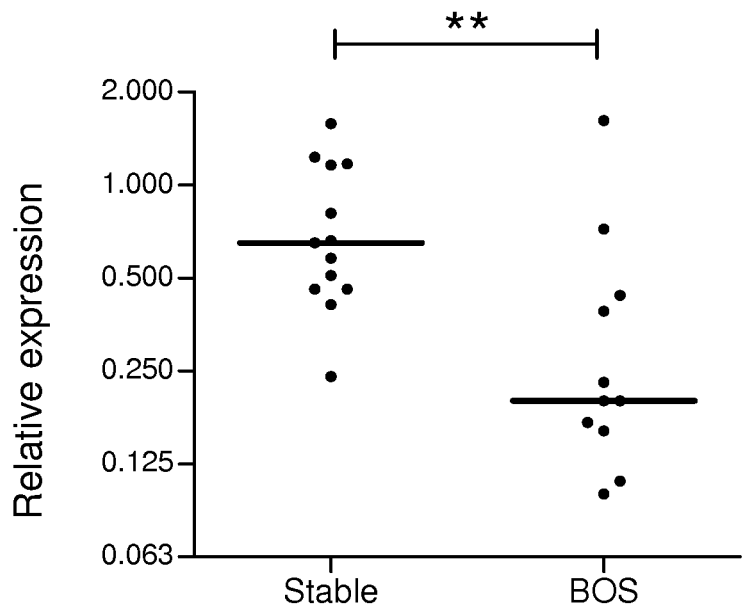

The invention is in the field of lung transplantation, particularly, the invention allows to identify whether a subject is at risk of developing bronchiolitis obliterans syndrome.

BACKGROUND OF THE INVENTION

Chronic lung allograft dysfunction (CLAD) is the main limitation of long-term survival after lung transplantation. CLAD manifest mainly by an abnormal remodeling of the small airways resulting in progressive airflow obstruction called Bronchiolitis Obliterans Syndrome (BOS) (1-3). A restrictive ventilatory process referred as Restrictive Allograft Syndrome (RAS) has been described recently as another form of CLAD (4). The prevalence of CLAD reaches 50% at 5 years (35% BOS and 15% RAS) of lung transplant recipients. Its late diagnosis, based upon the decline of lung function, reveals an advanced degradation of the allograft. Prognosis is poor, with respectively 4 and 2 years median survival for BOS and RAS after onset. Identification of harbingers of CLAD in lung transplant recipients is thus necessary to allow proactive and targeted strategies to harness the progression of the disease, before irreversible degradation of the allograft.

It is hypothesized that CLAD arises from repeated injuries from both alloimmune and non-alloimmune mechanisms, generating fibrosis and airway obstruction (5). Tracking these inflammation and fibrotic processes has long been used to identify early signs of the disease. BAL neutrophilia, levels of regulatory T cells, chemokines/cytokines or matrix metalloproteases (MMP) have thus been suggested as early biomarkers of CLAD (6-10). More recently, expression profiling of lung biopsies pinpointed fibrosis-associated genes for the diagnosis or the prediction of CLAD (11). Yet, these invasive lung-centered approaches remained hampered by the accessibility to biological samples and are therefore limited for a routine monitoring of LTR. In blood, circulating fibrocytes or cytokine concentration have been proposed as potential biomarkers (12-15). However, these studies concerned a limited number of patients and confirmation in follow-up studies are still missing. Consequently, none of these attempts have demonstrated yet enough feasibility and robustness to achieve clinical acceptance. Accordingly, there is a need to identify new methods that allows to explore CLAD and provide early biomarkers of CLAD.

SUMMARY OF THE INVENTION

The invention relates to a method for predicting the risk of having CLAD in a subject comprising the following steps:
 i) measuring the expression level of POU2AF1 or BLK in a biological sample obtained from said subject;
 ii) comparing the expression level of POU2AF1 or BLK with a predetermined reference value and
 iii) concluding that the subject is at risk of having CLAD when the expression level of POU2AF1 or BLK is lower than the predetermined reference value or concluding that the subject is not at risk of having CLAD when the expression level of POU2AF1 or BLK is higher than the predetermined reference value. In particular, the present invention is defined by the claims.

DETAILED DESCRIPTION OF THE INVENTION

Inventors of the present invention have used a large-scale gene expression profiling of whole blood to identify early biomarkers of CLAD. Microarray experiments performed from 80 patients (40 stable and 40 BOS) identify 47 genes differentially expressed between the stable and the BOS groups. An independent set of patients (13 stable, 11 BOS) was then used for an external validation by QPCR. POU Class 2 Associating Factor 1 (POU2AF1) and B-cell lymphocyte kinase (BLK) genes were confirmed as predictive markers of BOS more than 6 months before the clinical diagnosis.

Method for Predicting the Risk of Having CLAD in a Subject

Accordingly, in a first aspect, the invention relates to a method for predicting the risk of having CLAD in a subject comprising the following steps: i) measuring the expression level of POU2AF1 or BLK in a biological sample obtained from said subject; ii) comparing the expression level of POU2AF1 or BLK with a predetermined reference value and iii) concluding that the subject is at risk of having CLAD when the expression level of POU2AF1 or BLK is lower than the predetermined reference value or concluding that the subject is not at risk of having CLAD when the expression level of POU2AF1 or BLK is higher than the predetermined reference value.

As used herein, the term "predicting" means that the subject to be analyzed by the method of the invention is allocated either into the group of subjects who will have CLAD, or into a group of subjects who will not have CLAD. Having CLAD referred to in accordance with the invention, particularly, means that the subject will have higher risk to develop CLAD. Typically, said risk is elevated as compared to the average risk in a cohort of transplanted subjects. In the context of the invention, the risk of having CLAD in a subject shall be predicted. The term "predicting the risk", as used herein, refers to assessing the probability according to which the patient as referred to herein will have CLAD. As will be understood by those skilled in the art, such an assessment is usually not intended to be correct for 100% of the subjects to be investigated. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the invention allows that the prediction of an increased risk will be correct for at least 60%, at least 70%, at least 80%), or at least 90% of the subjects of a given cohort or population. The term, preferably, relates to predicting whether or not there is an increased risk of having CLAD compared to the average risk of CLAD in a population of subjects rather than giving a precise probability for the said risk.

As used herein, the term "CLAD" refers to chronic lung allograft dysfunction. CLAD is the main limitation of long term survival after lung transplantation. The prevalence of CLAD is around 50% at 5 years (35% for the BOS and 15% for the RAS phenotype). Its late diagnosis, based upon the decline of the lung functions, reveals an advanced degradation of the allograft. Prognosis is poor, with respectively 4 and 2 years median survival for BOS and RAS phenotype after disease onset.

In a particular embodiment, the method according to the invention is suitable to predict the risk of having BOS. As used herein, the term "BOS" refers to bronchiolitis obliterans syndrome. It is the main CLAD subtype. It refers to a lung disorder that is mainly associated with chronic allograft dysfunction after lung transplantation. BOS is characterized by inflammation and fibrosis of bronchiolar walls that reduce the diameter of the bronchioles and result in progressive and irreversible airflow obstruction.

In a particular embodiment, the method is suitable to predict the risk of having RAS. As used herein, the term "RAS" refers to restrictive allograft syndrome (RAS). RAS is characterized by a stair-step progression pattern, with tissue damage and fibrotic lesions occurring in the periphery of the lungs (ie, in the visceral pleura, in the alveolar interstitium and in the interlobular septa), resulting in a reduction of total lung capacity.

As used herein, the term "subject" refers to any mammals, such as a rodent, a feline, a canine, and a primate. Particularly, in the present invention, the subject is a human. In a particular embodiment, the subject is a transplanted subject. As used herein, the term "transplanted subject" also called as grafted subject, refers to a subject who has received an organ transplantation. The term "organ transplantation" refers to the procedure of replacing diseased organs, parts of organs, or tissues by healthy organs or tissues. The transplanted organ or tissue can be obtained either from the subject himself (=autograft), from another human donor (=allograft) or from an animal (=xenograft). Transplanted organs may be artificial or natural, whole (such as kidney, heart, lung and liver) or partial (such as heart valves, lung, skin and bone). In a particular embodiment, the subject is a lung transplanted subject. In particular, said lung transplanted subject may further have been grafted with the liver or the kidney, of the lung donor or of a non-related donor.

As used herein, the term "expression level" refers to the expression level of each of the 2 genes with further other values corresponding to the clinical parameters. Typically, the expression level of the 2 genes may be determined by any technology known by a person skilled in the art. In particular, each gene expression level may be measured at the genomic and/or nucleic and/or protein level. In a particular embodiment, the expression level of gene is determined by measuring the amount of nucleic acid transcripts of each gene. In another embodiment, the expression level is determined by measuring the amount of each gene corresponding protein. The amount of nucleic acid transcripts can be measured by any technology known by a man skilled in the art. In particular, the measure may be carried out directly on an extracted messenger RNA (mRNA) sample, or on retrotranscribed complementary DNA (cDNA) prepared from extracted mRNA by technologies well-known in the art. From the mRNA or cDNA sample, the amount of nucleic acid transcripts may be measured using any technology known by a man skilled in the art, including nucleic microarrays, quantitative PCR, microfluidic cards, and hybridization with a labelled probe. In a particular embodiment, the expression level is determined using quantitative PCR.

Quantitative, or real-time, PCR is a well-known and easily available technology for those skilled in the art and does not need a precise description. Methods for determining the quantity of mRNA are well known in the art. For example the nucleic acid contained in the biological sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous. Other methods of amplification include ligase chain reaction (LCR), transcription-mediated amplification (TMA), strand displacement amplification (SDA) and nucleic acid sequence based amplification (NASBA). Nucleic acids having at least 10 nucleotides and exhibiting sequence complementarity or homology to the mRNA of interest herein find utility as hybridization probes or amplification primers. It is understood that such nucleic acids do not need to be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin). Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate). The nucleic acid primers or probes used in the above amplification and detection method may be assembled as a kit. Such a kit includes consensus primers and molecular probes. A kit also includes the components necessary to determine if amplification has occurred. The kit may also include, for example, PCR buffers and enzymes; positive control sequences, reaction control primers; and instructions for amplifying and detecting the specific sequences. In a particular embodiment, the method of the invention comprises the steps of providing total RNAs extracted from a biological sample and subjecting the RNAs to amplification and hybridization to specific probes, more particularly by means of a quantitative or semi-quantitative RT-PCR. In another embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a biological sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel (16).

As used herein, the term "biological sample" refers to any sample obtained from a transplanted subject, such as a serum sample, a plasma sample, a urine sample, a blood sample, a lymph sample, or a tissue biopsy. In a particular embodiment, biological samples for the determination of an expression level include samples such as a blood sample, a lymph sample, or a biopsy. In a particular embodiment, the biological sample is a blood sample, more particularly, peripheral blood mononuclear cells (PBMC). Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis, which will preferentially lyse red blood cells. Such procedures are known to the experts in the art.

As used herein, the term "POU2AF1" refers to POU Class 2 Associating Factor 1. The naturally occurring human POU2AF1 gene has a nucleotide sequence as shown in Genbank Accession number NM_006235 and the naturally occurring human POU2AF1 protein has an aminoacid sequence as shown in Genbank Accession number NP_006226.2. The murine nucleotide and amino acid sequences have also been described (Genbank Accession numbers NM_011136.2 and NP_035266.1).

As used herein, the term "BLK" refers to B-cell lymphocyte kinase. The protein BLK encoded by BLK gene and has a role in B-cell receptor signaling and B-cell development. The naturally occurring human BLK gene has a nucleotide sequence as shown in Genbank Accession number NM_001715.2 and the naturally occurring human BLK protein has an aminoacid sequence as shown in Genbank Accession number NP_001706.2. The murine nucleotide and amino acid sequences have also been described (Genbank Accession numbers NM_007549.2 and NP_031575.2).

As used herein, the term "predetermined reference value" refers to a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the selected peptide in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher is the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

Method for Preventing the Risk of Having CLAD

In a second aspect, the invention relates to a method for preventing the risk of having CLAD in a subject comprising a step of administering to said subject a therapeutically amount of immunosuppressive drugs.

In the context of the invention, the term "preventing the risk" or "prophylactic treatment" as used herein, refers to treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder.

As used herein, the term "subject" corresponds to the subject as described above. Typically, the subject is a transplanted subject. More particularly, the subject is a lung transplanted subject. In a particular embodiment, the subject is susceptible to have BOS. In another embodiment, the subject is susceptible to have RAS.

As used herein, the term "immunosuppressive drugs" also known as immunosuppressive agents or antirejection medications are drugs that inhibit or prevent the activity of immune system. Typically, the subject is treated with immunosuppressive drugs or other drugs that are currently known in the art or that will be identified in the future. In a particular embodiment, the subject is under immunosuppressive treatment, which means that the subject is administered with one or more immunosuppressive drugs. Immunosuppressive drugs that may be employed in transplantation procedures include corticosteroids, calcineurin inhibitors (cyclosporin, tacrolimus), azathioprine, mycophenolate mofetil and tyrosin kinase inhibitors (everolimus, sirolimus). These drugs may be used in monotherapy or in combination therapies. In the case of lung transplantation, the following immunosuppressive protocols are usually used. Subjects with primary lung transplantation receive an induction treatment. Protocols varies largely among centers worldwide but usually includes either injections of ATG (anti-thymocyte globulin) or basiliximab (other options are anti CD3 and anti CD5 antibodies), high dose of corticosteroids (>1 mg/kg/day), a calcineurin inhibitor and a fourth immunosuppressive treatment (MMF or Azathioprine) or an association of high dose of corticosteroids, calcineurin inhibitors and a third immunosuppressive treatment (MMF or azathioprine). Corticotherapy is then progressively tapered to a lifelong low maintenance dose (e.g. 5 to 10 mg/day).

In a particular embodiment, the method according to the invention comprises i) determining whether the subject is at risk of having CLAD by the method as described above and ii) administering to said subject a therapeutically amount of immunosuppressive drugs when the expression level of POU2AF1 or BLK is lower than the predetermined reference value. Typically, the subject is administered with an increase therapeutically amount of immunosuppressive drugs.

In a particular embodiment, the method according to the invention is suitable to prevent the risk of having BOS.

A Method for Immunosuppressive Therapy Weaning

In a third aspect, the invention relates to a method for identifying a subject under immunosuppressive therapy as a candidate for immunosuppressive therapy weaning or minimization, comprising the steps of: i) determining whether the subject is at risk of having CLAD by the method as described above; and ii) concluding that the subject is eligible to immunosuppressive therapy weaning or minimization when the subject is not at risk of CLAD.

In a particular embodiment, the method according to the invention, wherein, the subject is at risk of having BOS.

In a particular embodiment, the method according to the invention, wherein, the subject is at risk of having RAS.

As used herein, the term "immunosuppressive therapy weaning or minimization" refers to the progressive reduction, and optionally eventually the suppression of an immunosuppressive therapy.

Kit

In another aspect, the present invention relates to a kit for determining whether a subject is at risk of having CLAD comprising at least one reagent for the determination of an expression level comprising the following genes: POU2AF1 or BLK.

As used herein, the term "a reagent for the determination of an expression level" is meant a reagent which specifically allows for the determination of said expression level, i.e. a reagent specifically intended for the specific determination of the expression level of the genes comprised in the expression profile. This definition excludes generic reagents useful for the determination of the expression level of any gene, such as taq polymerase or an amplification buffer, although such reagents may also be included in a kit according to the invention.

In some embodiments, the kit according to the invention may comprise instructions for determining whether a subject is at risk of having CLAD. The instructions for determining whether a subject is at risk of having CLAD (BOS or RAS) may include at least one reference expression profile. In a particular embodiment, at least one reference expression profile is a stable expression profile. Alternatively, at least one reference expression profile may be a graft non-tolerant expression profile (e.g. expression profile obtained from a healthy subject).

The invention will be further illustrated by the following figures and examples. However, these examples and figures should not be interpreted in any way as limiting the scope of the present invention.

FIGURES

FIG. 1. POU2AF1 as a predictive marker of Bronchiolitis Obliterans Syndrome. POU2AF1 expression determined by qPCR was compared between stable and BOS patients. (A) POU2AF1 expression was lower in BOS patients 6 months or more before CLAD diagnosis (stable vs LTP class, p<0.01). (B) ROC curve indicated that POU2AF1 expression discriminated well stable from BOS patients with an AUC of 0.8322 (95% CI=0.6382 to 1.026). (C) Kaplan-Meier analysis of BOS-free survival categorized by level of POU2AF1 expression.

FIG. 2. BLK as a predictive marker of Bronchiolitis Obliterans Syndrome. (A) BLK expression determined by QPCR was compared between stable and BOS patients. (B) ROC curve indicated that BLK expression discriminated well stable from BOS patients (AUC=0.7797, 95% CI=0.5688 to 0.9907). (C) Kaplan-Meier analysis of BOS-free survival categorized by level of BLK expression.

EXAMPLE

Material & Methods

Patients

Lung transplant recipients were recruited within the multicentre COLT (Cohort in Lung Transplantation, NCT00980967) study (Comité de Protection des Personnes Ouest 1-Tours, 2009-A00036-51). Study was approved by local ethical committee and all participants provided written informed consent. From September 2009 to October 2013, 1180 patients were included for 1024 transplantation. Inclusion criteria was at least 2 years of follow-up unless the diagnosis of CLAD was made before. The minimum follow up time for stable patients was 3 years. Patients with insufficient follow up, patients who die or patients retransplanted within 2 years were excluded. The eligible patients (n=688) were phenotyped by a blind adjudication committee based upon pulmonary function tests and chest imaging according to ISHLT/ERS/ATS guidelines (1, 19, as already published (20, 21)). Two hundred and sixty-five patients were excluded because of other phenotypes or confounding factors, 338 stable patients and 85 BOS patients were identified. Stable and BOS patients were then selected based upon sample availability, absence of infection or acute rejection within one month before or after blood collection and the quality of RNA. For the identification set, 49 stables and 40 BOS patients were used. Twenty five independent patients (13 stable and 12 BOS) were included in the validation set.

RNA Isolation

Samples were collected in PAXgene tubes (PreAnalytix, Qiagen), and stored at −80° C. Total RNA was extracted using the PAXgene blood RNA system kit with an on-column DNase digestion protocol according to the manufacturer's instructions. Quantity and quality of total RNA were determined using a 2100 Bioanalyzer (Agilent Technologies Incorporation). Microarray and qPCR analyses were performed on RNA with a RNA integrity number (RIN) above 6.5.

Gene Expression Microarray Analysis

Cyanin-3 and cyanin-5 labelled RNA were prepared with 100 ng of total RNA using the Two Color Agilent Low Input Quick Amp Labeling Kit following the manufacturer's instructions (Agilent Technologies Inc, Palo Alto, Calif., USA). The labeled cRNA samples were hybridized on SurePrint G3 Human Gene Expression v3 8×60K Microarrays (Agilent). Data extraction of median feature intensity was performed with Feature Extraction software v10.7 (Agilent Technologies). In order to remove signal intensity bias between each array, median feature intensities were normalized with the lowess (locally weighted scatterplot smoothing) method, then spots for which half of the samples exhibited a signal less than the mean of all median signals were removed. A batch effect correction was performed with Combat algorithm on the 28,867 remaining spots. Normalized microarray data were deposited in the Gene Expression Ominbus (GEO) database (accession number GSE94557).

For identification of differential genes, Student's t-test was performed comparing STA group and each group of interest with bootstrap resampling (1,000 times). Due to bootstrap's pessimistic bias, genes with mean of p-values inferior to 5% and fold change superior to 1.5 was considered as differentially expressed. The biological significance of selected genes was assessed using GOminer software. Only GO categories enriched with a false discovery rate (FDR) inferior to 5% and with at least 5 represented genes were selected. The cell type source of differential genes was evaluated using the gene set enrichment analysis web tool Enrichr (22).

Quantitative PCR (qPCR) for Microarray Validation

Microarray results were validated by qPCR with a set of independent samples. After reverse transcription with Superscript III (Invitrogen) real-time quantitative PCR was performed on a Taqman StepOne plus real time PCR system (Applied Biosystems) using commercially available primers: HPRT1 (Hs99999909_m1), β2M(Hs00984230_m1), ACTB (Hs99999903_m1), DEFA4 (Hs01056651_g1), ELANE (Hs00975994_g1), AZU1 Hs00156049_m1, FCRL6 (Hs02341772_m1), IGLL5 (Hs04330879_u1), POU2AF1 (Hs01573371_m1), CTSL1 (Hs00964650_m1), KRLC3 (Hs01652462_m1), KRLC4 (Hs00255338_m1), BLK (Hs01017452_m1), DEFA3 (Hs00414018_m1) and OLFM4 (Hs00197437_m1). Samples were run in duplicate and the geometric mean of quantification cycle values (Cq) for HPRT1, β2M and ACTB was used for normalization. Relative expression between a sample and a reference was calculated according to the 2-ΔΔCq method.

Statistics

For QPCR experiments, the non-parametric Whitney test was applied using GraphPad Prism (Graphpad software, La Jolla, Calif., USA). *$p<0.05$, $p<0.01$, *$p<0.001$.

Results

Gene Expression Profiling of Whole Blood from Lung Transplant Recipients

Patients recruited within the multicentre COLT cohort were phenotyped as stable or BOS by a blind adjudication committee based upon pulmonary function tests and chest imaging according to ISHLT/ERS/ATS guidelines (1, 19). Inclusion criteria was at least 2 years of follow-up unless the diagnosis of CLAD was made before. Stable patients display no signs of CLAD for at least 3 years after lung transplantation. Stable and BOS patients were selected according to sample availability, absence of infection or acute rejection close to blood collection and quality of RNA. Two independent sets of patients were then prepared for the identification and the validation experiments. Patients groups were homogeneous regarding age, sex, BMI, type of transplantation, induction treatment and infection and rejection events.

Since patients were longitudinally followed, several blood samples at different time-point post transplantation could be obtained from one recipient. We thus organised samples to defined three classes depending on the time between blood collection and CLAD diagnosis (defined as the time-point with a decline of ≥20% in FEV1 from the baseline). Long-term outcome prediction (LTP) class combined blood samples collected more than 12 months before CLAD diagnosis; medium-term outcome prediction (MTP) class combined blood samples collected within the 12 months that precede CLAD diagnosis and samples collected at or after CLAD diagnosis were incorporated in the diagnosis class (D). No patient duplicates were included within each of these three classes. Total RNA extracted from blood samples collected or 12 months after lung transplantation were used for stable patients.

Identification of Gene Signatures Associated with CLAD

For gene expression microarray, RNA from 40 stable patients were compared with 65 RNA samples from 40 BOS patients (LTP class, n=18; MTP class, n=21 and D class, n=26). Gene expression profiling identified a total of 47 genes differently expressed between stable and BOS groups. Comparing the stable group with the D group, we highlighted 20 unique genes (26 probes) with significant differential expression and fold change superior to 1.5, allowing a partial discrimination of stable with D in principal component analysis. GO analysis revealed 6 genes associated with biological defense response (e.g. GO:0009617, response to bacterium, FDR<0.0001, GO:0006952, defense response, FDR=0.0018), namely alkaline phosphatase, liver/bone/kidney (ALPL, FC=0.40), azurocidin 1 (AZU1, FC=0.52), defensin alpha 3 (DEFA3, FC=0.41), defensin alpha 4 (DEFA4, FC=0.44), elastase, neutrophil expressed (ELANE FC=0.50) and peptidoglycan recognition protein 1 (PGLYRP1, FC=0.52).

Comparison between the stable and the MTP groups pinpointed 13 genes (16 probes) differentially expressed. Principal component analysis show a moderate discrimination between stable and MTP groups. While GO analysis showed no enrichment of biological ontology, likely due to the low number of genes, cell origin analysis using Enrichir enrichment analysis highlighted 3 genes significantly associated with B cells, i.e. B lymphoid tyrosine kinase (BLK, FC=0.62), chemokine (C—X—C motif) receptor 5 (CXCR5, FC=0.64) and POU class 2 associating factor 1 (POU2AF1, FC=0.56). Interestingly, unsupervised hierarchical clustering revealed that these 3 genes resided in the same cluster, along with B-cell related genes such as CD19, MS4A1, BANK1 and C40, suggesting the potential association of B-cell related gene expression with MTP.

Finally, 24 genes (48 probes) were identified when comparing stable with LTP groups. Stable and LTP groups were discriminated in principal component analysis (. GO analysis highlighted the enrichment of 7 genes related to the immune system (GO:0006955, immune response, FDR=0.022; GO:0002376 immune system process, FDR=0.039 and GO:0006952 defense response, FDR=0.073). Enrichr analysis stressed the enrichment of genes related to CD56+NK cells including granzyme A (GZMA, FC=1.62), granzyme B (GZMB, FC=1.67) and the killer cell lectin-like receptor subfamily C, member 3 (KLRC3, FC=1.50) and 4 (KLRC4, FC=1.56). Interestingly, BLK, immunoglobulin lambda-like polypeptide 5 (IGLL5) and POU2AF1 were associated with both MTP and LTP suggesting their potential as predictive biomarkers.

Validation of POU2AF1 and BLK as Predictive Biomarkers of CLAD

Figure 1B:
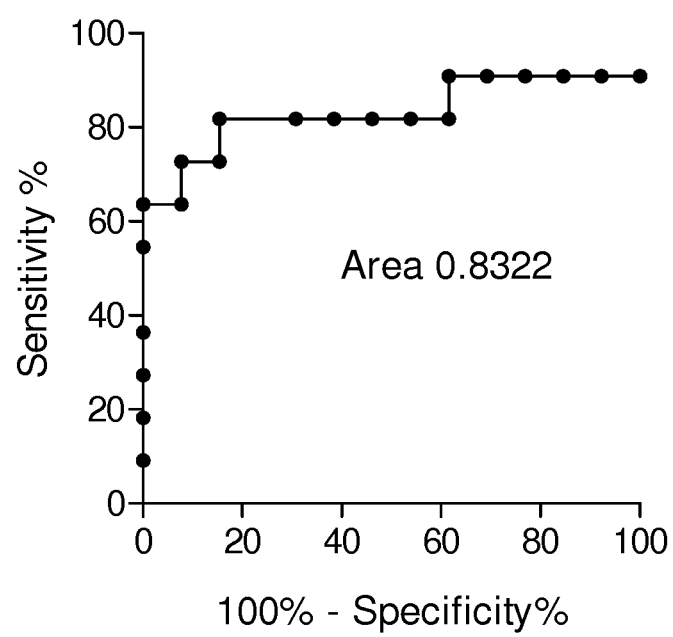
Figure 1C:
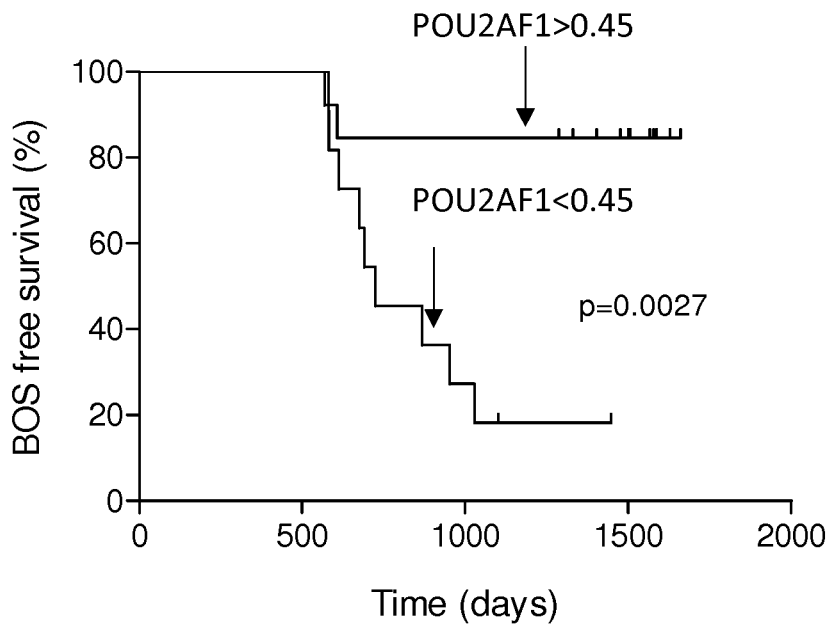
Figure 2A:
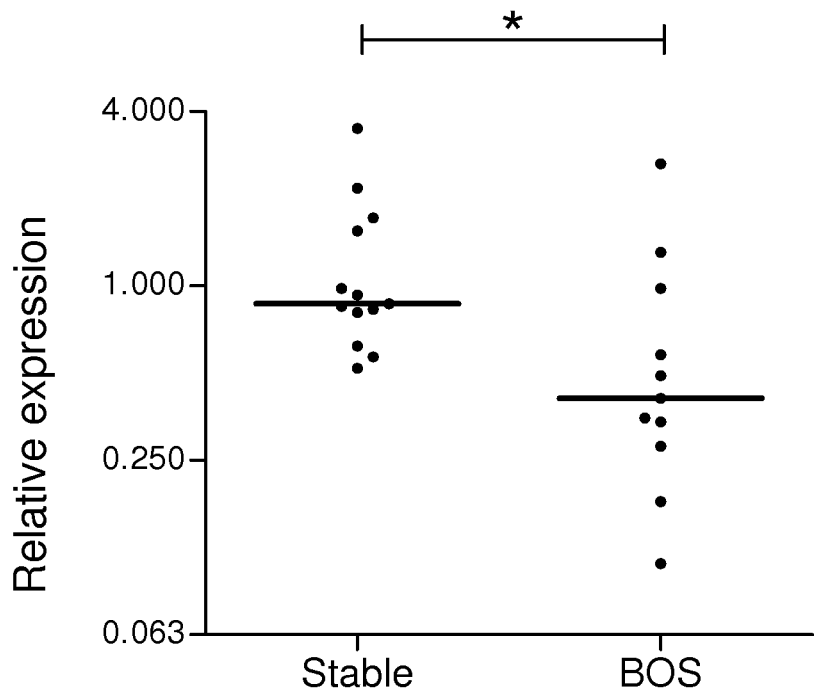
Figure 2B:
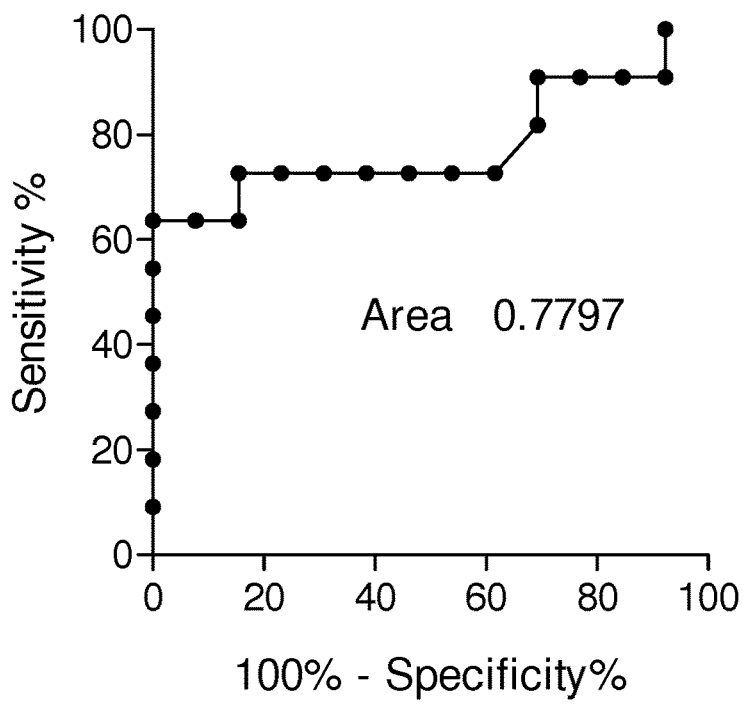
Figure 2C:
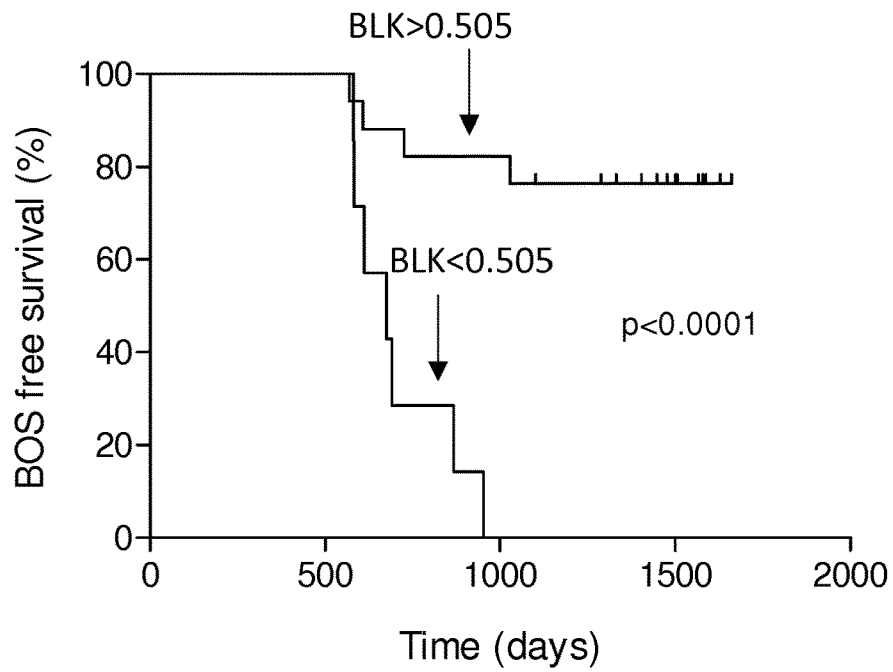

Based on their predictive values, biological functions, p-value and FC superior to 1.5, we selected 8 genes that were then tested by qPCR on an independent set of patients. We investigated here the overall predictive value of the selected genes, irrespective of time between blood collection and CLAD diagnosis, by pooling LTP and MTP class samples. qPCR experiments were performed on 13 stables samples and 11 BOS samples. Downregulation of POU2AF1 expression 6 months or more before CLAD diagnosis was validated by QPCR (p-value<0.01, FC=0.51) (FIG. 1A). ROC curve indicated that POU2AF1 expression discriminated well stable from BOS patients with an AUC of 0.8322 (95% CI=0.6382 to 1.026) (FIG. 1B). Noteworthy, expression of POU2AF1 in stable patients was constant between V3 and V4 (6 and 12 months post transplantation). Regarding BLK expression, we noted a reduced level of BLK expression in the BOS group (p<0.05, FC=0.56), 6 months or more before CLAD was diagnosed (FIG. 2A). ROC curve show a fair discrimination between the two groups of patients (AUC=0.7797, 95% CI=0.5688 to 0.9907) (FIG. 2B). As for POU2AF1, expression of BLK in stable patient was constant in time. The differential expression of the other 6 selected genes were not confirmed by qPCR. We finally performed Kaplan-Meier analyses to investigate the BOS free survival regarding POU2AF1 (FIG. 1C) and BLK (FIG. 2C) expression. The levels of POU2AF1 or BLK under 0.45 or 0.505 respectively reduced significantly the likelihood of BOS-free survival after lung transplantation.

REFERENCES

Throughout this application, various references describe the state of the art to which this invention pertains. The disclosures of these references are hereby incorporated by reference into the present disclosure.

1. Meyer K C, Raghu G, Verleden G M, Corris P A, Aurora P, Wilson K C, Brozek J, Glanville A R, ISHLT/ATS/ERS BOS Task Force Committee, ISHLT/ATS/ERS BOS Task Force Committee. An international ISHLT/ATS/ERS clinical practice guideline: diagnosis and management of bronchiolitis obliterans syndrome. *Eur Respir J* 2014; 44:1479-1503.
2. Koutsokera A, Royer P-J, Fritz A, Benden C, Tissot A, Aubert J-D, Antonietti J-P, Botturi-Cavaillès K, Magnan A, Pison C, Nicod L P. Risk factors for chronic lung allograft dysfunction (CLAD) in the SysCLAD cohort. *Eur Respir J* 2015; 46:PA1800.
3. Sato M. Chronic lung allograft dysfunction after lung transplantation: the moving target. *Gen Thorac Cardiovasc Surg* 2013; 61:67-78.
4. Sato M, Waddell T K, Wagnetz U, Roberts H C, Hwang D M, Haroon A, Wagnetz D, Chaparro C, Singer L G, Hutcheon M A, Keshavjee S. Restrictive allograft syndrome (RAS): a novel form of chronic lung allograft dysfunction. *J Heart Lung Transplant* 2011; 30:735-742.
5. Sato M, Keshavjee S. Bronchiolitis obliterans syndrome: alloimmune-dependent and -independent injury with aberrant tissue remodeling. *Semin Thorac Cardiovasc Surg* 2008; 20:173-182.
6. Devouassoux G, Drouet C, Pin I, Brambilla C, Brambilla E, Colle P-E, Pison C, Grenoble Lung Transplant Group. Alveolar neutrophilia is a predictor for the bronchiolitis obliterans syndrome, and increases with degree of severity. *Transpl Immunol* 2002; 10:303-310.
7. Neurohr C, Huppmann P, Samweber B, Leuschner S, Zimmermann G, Leuchte H, Baumgartner R, Hatz R, Frey L, Ueberfuhr P, Bittmann I, Behr J, Munich Lung Transplant Group. Prognostic value of bronchoalveolar lavage neutrophilia in stable lung transplant recipients. *J Heart Lung Transplant Off Publ Int Soc Heart Transplant* 2009; 28:468-474.
8. Hübner R H, Meffert S, Mundt U, Böttcher H, Freitag S, El Mokhtari N E, Pufe T, Hirt S, Folsch U R, Bewig B. Matrix metalloproteinase-9 in bronchiolitis obliterans syndrome after lung transplantation. *Eur Respir J* 2005; 25:494-501.
9. Bhorade S M, Chen H, Molinero L, Liao C, Garrity E R, Vigneswaran W T, Shilling R, Sperling A, Chong A, Alegre M-L. Decreased percentage of CD4+FoxP3+ cells in bronchoalveolar lavage from lung transplant recipients correlates with development of bronchiolitis obliterans syndrome. *Transplantation* 2010; 90:540-546.
10. Reynaud-Gaubert M, Marin V, Thirion X, Farnarier C, Thomas P, Badier M, Bongrand P, Giudicelli R, Fuentes P. Upregulation of chemokines in bronchoalveolar lavage fluid as a predictive marker of post-transplant airway obliteration. *J Heart Lung Transplant* 2002; 21:721-730.
11. Jonigk D, Izykowski N, Rische J, Braubach P, Kühnel M, Warnecke G, Lippmann T, Kreipe H, Haverich A, Welte T, Gottlieb J, Laenger F. Molecular Profiling in Lung Biopsies of Human Pulmonary Allografts to Predict Chronic Lung Allograft Dysfunction. *Am J Pathol* 2015; 185:3178-3188.
12. Shah R J, Bellamy S L, Lee J C, Cantu E, Diamond J M, Mangalmurti N, Kawut S M, Ware L B, Christie J D. Early plasma soluble receptor for advanced glycation end-product levels are associated with bronchiolitis obliterans syndrome. *Am J Transplant Off J Am Soc Transplant Am Soc Transpl Surg* 2013; 13:754-759.
13. Salama M, Jaksch P, Andrukhova O, Taghavi S, Klepetko W, Aharinejad S. Endothelin-1 is a useful biomarker for early detection of bronchiolitis obliterans in lung transplant recipients. *J Thorac Cardiovasc Surg* 2010; 140:1422-1427.
14. Paantjens A W M, Kwakkel-van Erp J M, Van Ginkel W G J, Van Kessel D A, Van Den Bosch J M M, Van De Graaf E A, Otten H G. Serum thymus and activation regulated chemokine levels post-lung transplantation as a predictor for the bronchiolitis obliterans syndrome. *Clin Exp Immunol* 2008; 154:202-208.
15. LaPar D J, Burdick M D, Emaminia A, Harris D A, Strieter B A, Liu L, Robbins M, Kron I L, Strieter R M, Lau C L. Circulating fibrocytes correlate with bronchiolitis obliterans syndrome development after lung transplantation: a novel clinical biomarker. *Ann Thorac Surg* 2011; 92:470-477.
16. Hoheisel J D. Microarray technology: beyond transcript profiling and genotype analysis. *Nat Rev Genet* 2006; 7:200-210.
17. Chesné J, Danger R, Botturi K, Reynaud-Gaubert M, Mussot S, Stern M, Danner-Boucher I, Mornex J-F, Pison C, Dromer C, Kessler R, Dahan M, Brugière O, Le Pavec J, Perros F, Humbert M, Gomez C, Brouard S, Magnan A, COLT Consortium. Systematic analysis of blood cell transcriptome in end-stage chronic respiratory diseases. *PloS One* 2014; 9:e109291.
18. Herazo-Maya J D, Noth I, Duncan S R, Kim S, Ma S-F, Tseng G C, Feingold E, Juan-Guardela B M, Richards T J, Lussier Y, Huang Y, Vij R, Lindell K O, Xue J, Gibson K F, Shapiro S D, Garcia J G N, Kaminski N. Peripheral blood mononuclear cell gene expression profiles predict poor outcome in idiopathic pulmonary fibrosis. *Sci Transl Med* 2013; 5:205ra136.
19. Verleden G M, Raghu G, Meyer K C, Glanville A R, Corris P. A new classification system for chronic lung allograft dysfunction. *J Heart Lung Transplant* 2014; 33:127-133.
20. Koutsokera A, Royer P J, Antonietti J P, Fritz A, Benden C, Aubert J D, Tissot A, Botturi K, Roux A, Reynaud-Gaubert M L, Kessler R, Dromer C, Mussot S, Mal H, Mornex J-F, Guillemain R, Knoop C, Dahan M, Soccal P M, Claustre J, Sage E, Gomez C, Magnan A, Pison C, Nicod L P, Consortium T S. Development of a Multivariate Prediction Model for Early-Onset Bronchiolitis Obliterans Syndrome and Restrictive Allograft Syndrome in Lung Transplantation. *Front Med* 2017; 4.
21. Pain M, Royer P-J, Loy J, Girardeau A, Tissot A, Lacoste P, Roux A, Reynaud-Gaubert M, Kessler R, Mussot S, Dromer C, Brugière O, Mornex J-F, Guillemain R, Dahan M, Knoop C, Botturi K, Pison C, Danger R, Brouard S, Magnan A, COLT Consortium. T Cells Promote Bronchial Epithelial Cell Secretion of Matrix Metalloproteinase-9 via a C—C Chemokine Receptor Type 2 Pathway: Implications for Chronic Lung Allograft Dysfunction. *Am J Transplant Off J Am Soc Transplant Am Soc Transpl Surg* 2016; doi:10.1111/ajt.14166.
22. Kuleshov M V, Jones M R, Rouillard A D, Fernandez N F, Duan Q, Wang Z, Koplev S, Jenkins S L, Jagodnik K M, Lachmann A, McDermott M G, Monteiro C D, Gundersen G W, Ma'ayan A. Enrichr: a comprehensive gene set enrichment analysis web server 2016 update. *Nucleic Acids Res* 2016; 44:W90-97.

The invention claimed is:
1. A prognostic method for determining whether a subject is at risk of having Chronic Lung Allograft Dysfunction (CLAD) and preventing the risk, comprising:
   measuring the expression level of BLK in a biological sample obtained from the subject;
   comparing the expression level of BLK with a predetermined reference value;
   concluding that the subject is at risk of having CLAD when the expression level of BLK is lower than the predetermined reference value; and
   administering to the subject determined to be at risk a therapeutic amount of immunosuppressive drugs to prevent CLAD.
2. The method according to claim 1, wherein the subject is a subject who has had a lung transplant.
3. The method according to claim 1 further comprising:
determining whether the subject is at risk of having Bronchiolitis Obliterans Syndrome (BOS) when the expression level of BLK is lower than the predetermined reference value.
4. The method according to claim 1 further comprising:
   determining whether the subject is at risk of having Restrictive Allograft Syndrome (RAS) when the expression level of BLK is lower than the predetermined reference value.
5. A method for immunosuppressive therapy weaning or minimization for a subject under immunosuppressive therapy, comprising:
   measuring the expression level of BLK in a biological sample obtained from the subject;
   comparing the expression level of BLK with a predetermined reference value;
   concluding that the subject is not at risk of having CLAD when the expression level of BLK is higher than the predetermined reference value;
   concluding that the subject is eligible for immunosuppressive therapy weaning or minimization; and then
   administering to the subject determined not to be at risk of having CLAD a progressive reduction of a therapeutic amount of immunosuppressive drugs to prevent CLAD.
6. The method according to claim 1, wherein the subject is susceptible to have BOS.
7. The method according to claim 1, wherein the subject is susceptible to have RAS.

* * * * *